(12) United States Patent
Kubo et al.

(10) Patent No.: US 9,526,841 B2
(45) Date of Patent: Dec. 27, 2016

(54) SPRAYING DEVICE

(75) Inventors: Tomohiko Kubo, Osaka (JP); Teruhisa Hirobe, Osaka (JP)

(73) Assignee: NIPRO CORPORATION, Osaka (JP)

( * ) Notice: Subject to any disclaimer, the term of this patent is extended or adjusted under 35 U.S.C. 154(b) by 0 days.

(21) Appl. No.: 13/807,592

(22) PCT Filed: Jun. 28, 2011

(86) PCT No.: PCT/JP2011/064831
§ 371 (c)(1),
(2), (4) Date: Dec. 28, 2012

(87) PCT Pub. No.: WO2012/002398
PCT Pub. Date: Jan. 5, 2012

(65) Prior Publication Data
US 2013/0096493 A1 Apr. 18, 2013

(30) Foreign Application Priority Data
Jun. 30, 2010 (JP) .................................. 2010-148432

(51) Int. Cl.
*A61M 5/315* (2006.01)
*A61M 15/08* (2006.01)
(Continued)

(52) U.S. Cl.
CPC ......... *A61M 5/3155* (2013.01); *A61M 3/0262* (2013.01); *A61M 5/3129* (2013.01);
(Continued)

(58) Field of Classification Search
CPC ... A61M 15/08; A61M 11/06; A61M 5/31595
(Continued)

(56) References Cited

U.S. PATENT DOCUMENTS 4,642,102 A * 2/1987 Ohmori .................. 604/210
4,962,868 A * 10/1990 Borchard .................. 222/49
(Continued)

FOREIGN PATENT DOCUMENTS

CN 1175217 A 3/1998
CN 201492765 U 6/2010
(Continued)

OTHER PUBLICATIONS

European Action dated Mar. 4, 2015.

*Primary Examiner* — Laura Bouchelle
*Assistant Examiner* — Anh Bui
(74) *Attorney, Agent, or Firm* — Birch, Stewart, Kolasch & Birch, LLP

(57) ABSTRACT

An administration device can discharge a prescribed, equal amount of medicine a number of times by spraying. A spraying device includes a barrel; a gasket provided slidably movable in liquid-tight manner in the barrel; a rod coupled to a base end of the gasket; and a regulating member provided on the barrel, having a projection that can slidably fit with the guide groove. The guide groove includes at least first and second continuous administering grooves. The second administering groove is configured to include a transitional portion extending in the circumferential direction with a groove wall on the base end side aligned with the base end of the first administering portion, and a second administering portion extending from the transitional portion to a base end along the longitudinal direction. An energizing protrusion engageable with the projection is provided at a boundary between the transitional portion and the second administering portion.

25 Claims, 16 Drawing Sheets

(51) Int. Cl.
*A61M 3/02* (2006.01)
*A61M 11/08* (2006.01)
*A61M 5/31* (2006.01)
*A61M 11/00* (2006.01)

(52) U.S. Cl.
CPC ...... *A61M 5/31576* (2013.01); *A61M 11/007* (2014.02); *A61M 11/08* (2013.01); *A61M 15/08* (2013.01); *A61M 5/31595* (2013.01); *A61M 2005/3139* (2013.01); *A61M 2210/0618* (2013.01)

(58) Field of Classification Search
USPC .................................................... 604/58, 210
See application file for complete search history.

(56) References Cited

U.S. PATENT DOCUMENTS

| | | | | |
|---|---|---|---|---|
| 5,318,544 | A * | 6/1994 | Drypen | A61M 5/3155 604/210 |
| 6,174,304 | B1 | 1/2001 | Weston | |
| 6,478,779 | B1 | 11/2002 | Hu | |
| 8,523,806 | B2 * | 9/2013 | Hayakawa | 604/82 |
| 2002/0010428 | A1 * | 1/2002 | Vedrine | A61M 11/06 604/187 |
| 2002/0035349 | A1 * | 3/2002 | Jansen et al. | 604/82 |
| 2004/0210207 | A1 * | 10/2004 | Amisar | A61J 1/1412 604/415 |
| 2010/0057047 | A1 * | 3/2010 | Djupesland | A61M 15/0098 514/1.1 |
| 2010/0258115 | A1 | 10/2010 | Kawamura et al. | |
| 2011/0118701 | A1 * | 5/2011 | Baney | A61M 5/31595 604/506 |
| 2013/0197446 | A1 * | 8/2013 | Gustafsson et al. | 604/189 |

FOREIGN PATENT DOCUMENTS

| | | |
|---|---|---|
| EP | 0 611 035 A1 | 8/1994 |
| JP | 60-175249 U | 11/1985 |
| JP | 61-30699 U | 2/1986 |
| JP | 63-84239 U | 6/1988 |
| JP | 2-11158 A | 1/1990 |
| JP | 2004-49726 A | 2/2004 |
| JP | 3136169 U | 10/2007 |
| WO | WO 96/19252 A1 | 6/1996 |
| WO | WO 2009/057572 A1 | 5/2009 |
| WO | WO 2009/095735 A1 | 8/2009 |

* cited by examiner

SPRAYING DEVICE

TECHNICAL FIELD

The present invention relates to a spraying device. More specifically, the present invention relates to an appliance for administering medication by spraying.

BACKGROUND ART

Various manners and methods of administering medication have been known. By way of example, medicines related to immune system can be administered by hypodermic injection as well as by nasal administration. Nasal administration refers to a method of spraying, to each of the nasal cavities, a prescribed, equal amount of medicine, which method is suitably used as it causes no pain at the time of administration.

Nasal administration requires a number of administering operations as described above. For the operations, one administering apparatus may be used for each dose, suction and administration of medicine may be repeated, or a number of doses may be sucked at one time and the medicine may be discharged a number of times.

If one administering apparatus is used for each dose and the medication is to be administered a plurality of times, the user must prepare as many apparatuses as the number of doses, resulting in a considerable amount of waste. If medicine sucking and administering operations are repeated for each dose, it means that the suction and discharge of medicine must be done by the number of doses, which is rather burdensome for the user.

If a number of doses is sucked at one time and the medicine of a desired amount is administered a number of times, adjustment is required of the user to realize discharge of an exact amount of medicine each time, since the medicine must be discharged a number of times, each time by a prescribed amount. Conventionally, discharge of an exact amount of medicine relies on a scale provided on the apparatus. It is accepted as a given that adjustment is troublesome and requires excessive power of concentration. Further, since it relies on a scale, whether or not an exact amount of medicine has been discharged cannot be known. The discharged dosage may vary from time to time.

Patent Document 1 proposes, as an administering apparatus capable of dispensing a number of doses, a syringe that has a stopper receiver on a barrel and stoppers on a rod to regulate an amount of movement, so that a medicine can be discharged a number of times, each by a desired amount without relying on a scale. The syringe includes: a rod having a plurality of ribs provided at different positions in outer circumferential direction and stoppers different in length from a tip end of the rod formed on respective ribs; and a stopper receiver that engages with each stopper, provided on an outer cylinder. By rotating and moving forward the rod such that the stopper engages with the stopper receiver, an amount of medicine that corresponds to the stopper position can be discharged. After one stopper and the stopper receiver engage, by rotating and moving forward the rod again such that the stopper receiver engages with another stopper, further discharge of medicine becomes possible. Therefore, it is possible to discharge a medicine a number of times each by a determined amount, without relying on the scale.

CITATION LIST

Patent Document

Patent Document 1: Japanese Patent Laying-Open No. 2004-49726

SUMMARY OF INVENTION

Technical Problem

It is noted, however, that the syringe described in the prior art allows free rotation of the rod in the circumferential direction while the rod is moved to the tip end direction. Therefore, even if a stopper allowing discharge of a desired amount of medicine is aligned with the stopper receiver in the longitudinal direction before administration and then the rod is moved forward, it is possible that the rod rotates unintentionally, the expected engagement between the stopper and the stopper receiver fails, and eventually the rod is moved further forward and an excessive amount of medicine is discharged.

Further, after one stopper engages with the stopper receiver in the syringe, the rod is rotated such that the stopper receiver engages with another stopper, to further discharge the desired amount of medicine. During the rotation, however, it is possible that the rod unintentionally moves forward. By such an unintended forward movement of the rod, discharge of the medicine may be started, and the dosage may possibly become smaller than the originally intended amount.

Further, the syringe does not have any energizing means and does not have a structure that can apply pressure to the medicine when the medicine is pushed out. Namely, the syringe is not capable of spraying. Thus, though the syringe may be useful for injection, it is difficult to adopt this as a spraying device. Therefore, an object is to provide an administering device capable of discharging, by spraying, a medicine a number of times, each time by a prescribed equal amount.

Solution To Problem

Through intensive study, the inventors have arrived at the present invention as described below. Specifically, the present invention provides a spraying device for spraying liquid, including: a hollow barrel having a spray nozzle mounting portion formed at a tip end and a flange formed at a base end; a gasket provided slidably movable in liquid-tight manner in the barrel; a rod coupled to a base end of the gasket; a guide groove provided on the rod; and a regulating member, provided on the barrel, having an opening allowing passage of the rod formed at the center, and having a projection projecting from an edge of the opening to the center to be slidably fit with the guide groove; wherein the guide groove includes at least a first administering groove and a second administering groove provided continuous from the first administering groove; the first groove is configured to include a priming portion and a first administering portion extending from the priming portion to a base end along the longitudinal direction; the second administering groove is configured to include a transitional portion extending in the circumferential direction with a groove wall on the base end side aligned with the base end of the first administering groove, and a second administering portion extending from the transitional portion to the base end along the longitudinal direction; and an energizing protrusion engageable with the projection is provided at a boundary between the transitional portion and the second administering portion.

The priming portion may be a groove extending in the longitudinal direction, a groove extending in a circumferential direction, or an L-shaped groove having a tip end side extending in the longitudinal direction and a base end side extending in the circumferential direction. Preferably, an energizing protrusion engageable with the projection is provided at a boundary between the priming portion and the first administering portion.

Further, a rotation preventing protrusion engageable with the projection may be provided at a boundary between the first and second administering grooves.

The guide groove may include a third, fourth or further administering grooves. Each such administering groove may have the same structure as the second administering groove, including a transitional portion extending in the circumferential direction with a groove wall on the base end side aligned with the base end of the immediately preceding administering groove, and an administering portion extending from the transitional portion to the base end along the longitudinal direction and provided with an energizing protrusion engageable with the projection at a boundary between the transitional portion and the administering portion. A rotation preventing protrusion may additionally be provided.

The flange may have a housing portion capable of accommodating the regulating member, and the regulating member may be housed in the housing portion.

The regulating member may be structured to have, at a tip end, a housing portion capable of accommodating the flange therein, and a fixing portion engageable with an outer wall of the barrel, and may be attached by accommodating a lower end of the barrel.

A spray nozzle is mounted on the spray nozzle mounting portion, and the spray nozzle may contain powdered formulation.

Further, the device may have a medicament container adapter allowing communication between the barrel and another medicament container, detachably provided to cover the barrel.

In the spray type administering device as described above, the rod is provided with guide grooves; the outer cylinder has fixed thereon a projection that can slidably fit with the guide groove; the guide groove includes at least a first administering groove extending in the longitudinal direction, and a second administering groove extending from a base end of the first administering groove; and in each of the second and further administering grooves, an energizing protrusion is provided at an initial position for spraying. Therefore, unintended rotation while the rod is moved forward, preventing stoppage of the rod at the supposed position, can be avoided. Further, since the energizing protrusion is provided, movement of the rod in the longitudinal direction is prevented when the rod is rotated, and it can always be fixed at the initial position for administration. At the same time, the effect that the pressure for spraying is applied when the energizing protrusion is pushed with force, can be attained.

Advantageous Effects of Invention

The spraying device in accordance with the present invention is capable of spraying a medicine of a prescribed equal amount a number of times, simply by pushing the rod and, therefore, it can suitably be used for medical use.

DESCRIPTION OF EMBODIMENTS

Figure 1:
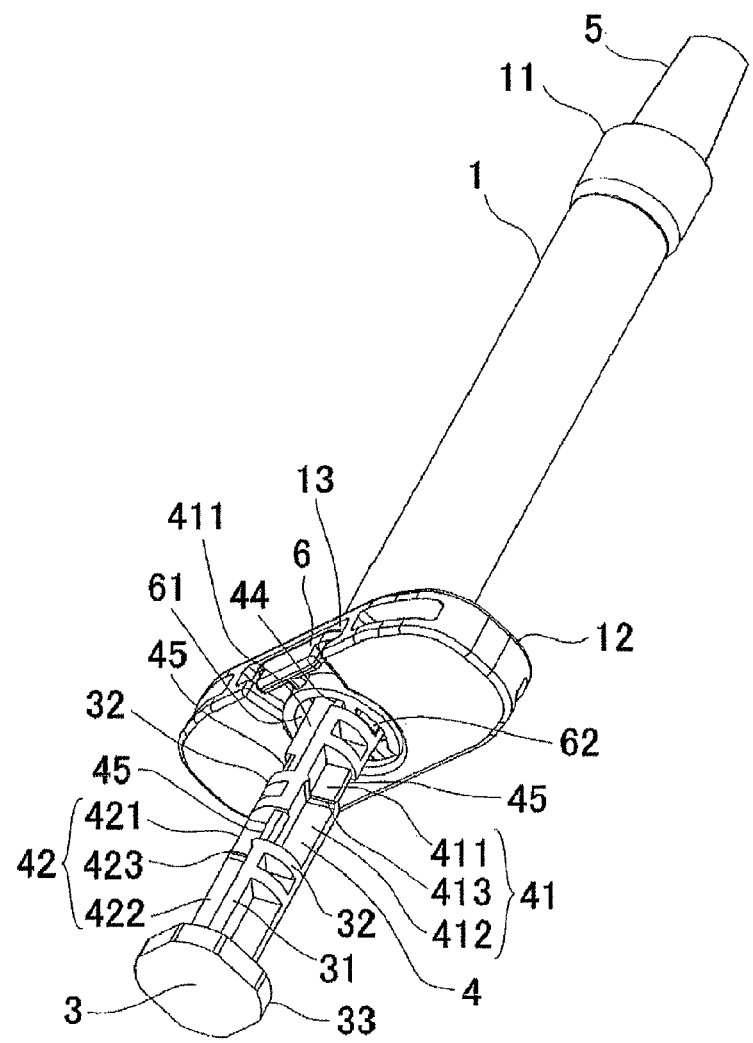
FIG. 1 is a perspective view showing a base end side of the spraying device in accordance with an embodiment of the present invention.

The spraying device in accordance with the present invention will be described with reference to the figures. The present invention, however, is not limited to the embodiments shown in the figures.

First, an embodiment of the present invention will be described with reference to FIGS. 1 to 3. A hollow barrel 1 has a Leur-Lock type spray nozzle connecting portion 11 formed at a tip end, and has a flange 12 at a base end. To spray nozzle connecting portion 11, a spray nozzle 5 is connected. In barrel 1, a gasket 2 that can slide and move in liquid-tight manner in barrel 1 is provided, and at the base end of gasket 2, a rod 3 formed integrally with gasket 2 is provided. An unbranched guide groove 4 is formed on rod 3, and guide groove 4 includes a first administering groove 41 and a second administering groove 42. The first administering groove is configured to include an L-shaped priming portion 411 extending from the tip end side along the longitudinal direction and then circumferential direction, and a first administering portion 412 extending from the priming portion 411 along the longitudinal direction to the base end. At the boundary between priming portion 411 and the first administering portion 412, a first energizing protrusion 413 is formed. The second administering groove 42 is formed continuous from the first administering portion 412. The second administering groove 42 is configured to include a transitional portion 421 extending in the circumferential direction and having a groove wall on the base end side aligned with the base end of the first administering portion 412, and a second administering portion 422 extending from the transitional portion 421 along the longitudinal direction to the base end. At the boundary between transitional portion 421 and the second administering portion 422, a second energizing protrusion 423 is formed. A regulating member housing 13 is provided on flange 12, and in regulating member housing 13, a regulating member 6, which is a C-shaped flat plate with an opening 61 for passing rod 3 formed at the center, is inserted through the open-side of the annular plate. A pair of arch-shaped columnar projections 62 that can slidably fit with the guide grooves 4 is formed, protruding from an edge of opening 61 to the central portion, to be opposite to each other, on regulating member 6.

Figure 2:
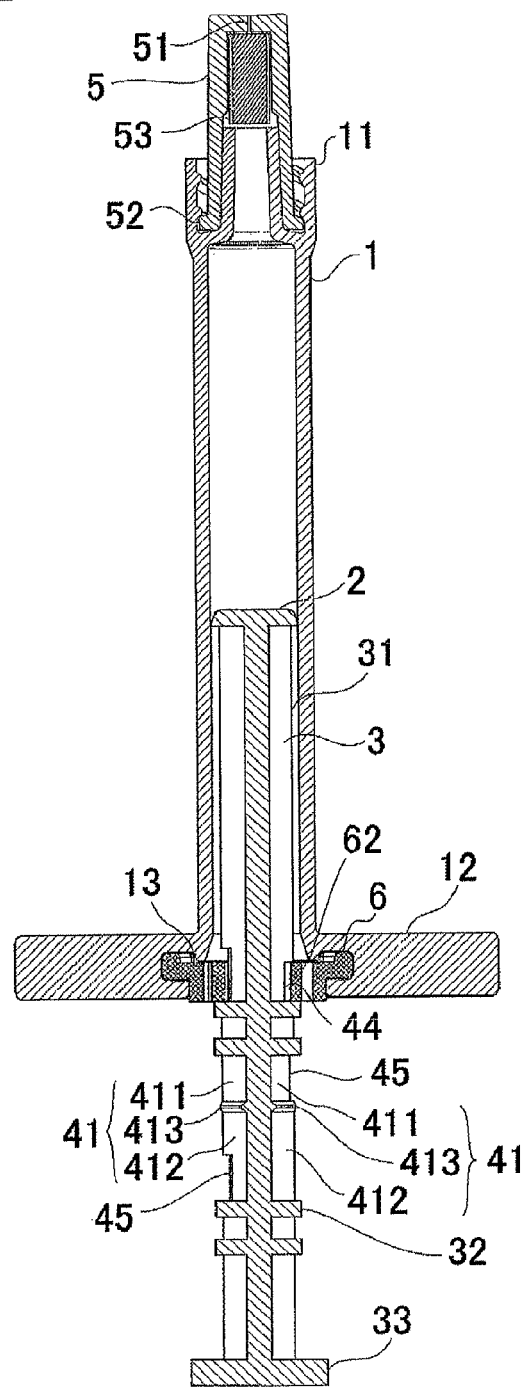
FIG. 2 is a vertical sectional view of the spraying device shown in FIG. 1.

In the rod of the spraying device illustrated in FIG. 1, the groove wall on the base end side at the transitional portion 421 is seemingly non-existent when the first administering groove 41 and the second administering groove 42 are placed next to each other. It is noted, however, that the presence of groove wall on the base end side of transitional portion 421 is simply unrecognizable, since the position of groove wall on the base end side of transitional portion 421 is the same as the position of second energizing protrusion 423.

Barrel 1 and gasket 2 may be formed of any material, provided that it does not react with the medicament in barrel 1 and that sliding movement in liquid-tight manner inside barrel 1 is ensured. Therefore, material generally used for medical equipment may be used. In the example of FIG. 1, gasket 2 and rod 3 are integrally formed of plastic. Besides, gasket 2 may be formed of an elastomer or rubber, and rod 3 formed of plastic may be coupled to its base end, as in the case of a general syringe.

Figure 4:
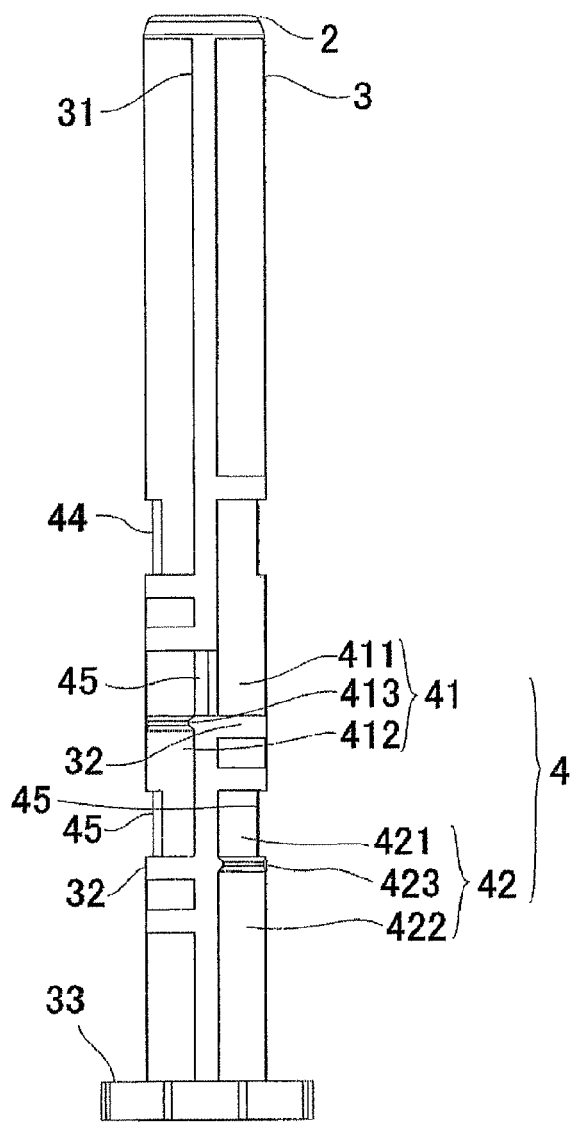
FIG. 4 shows the rod of FIG. 3 rotated by 45° about the central axis.
Figure 5:
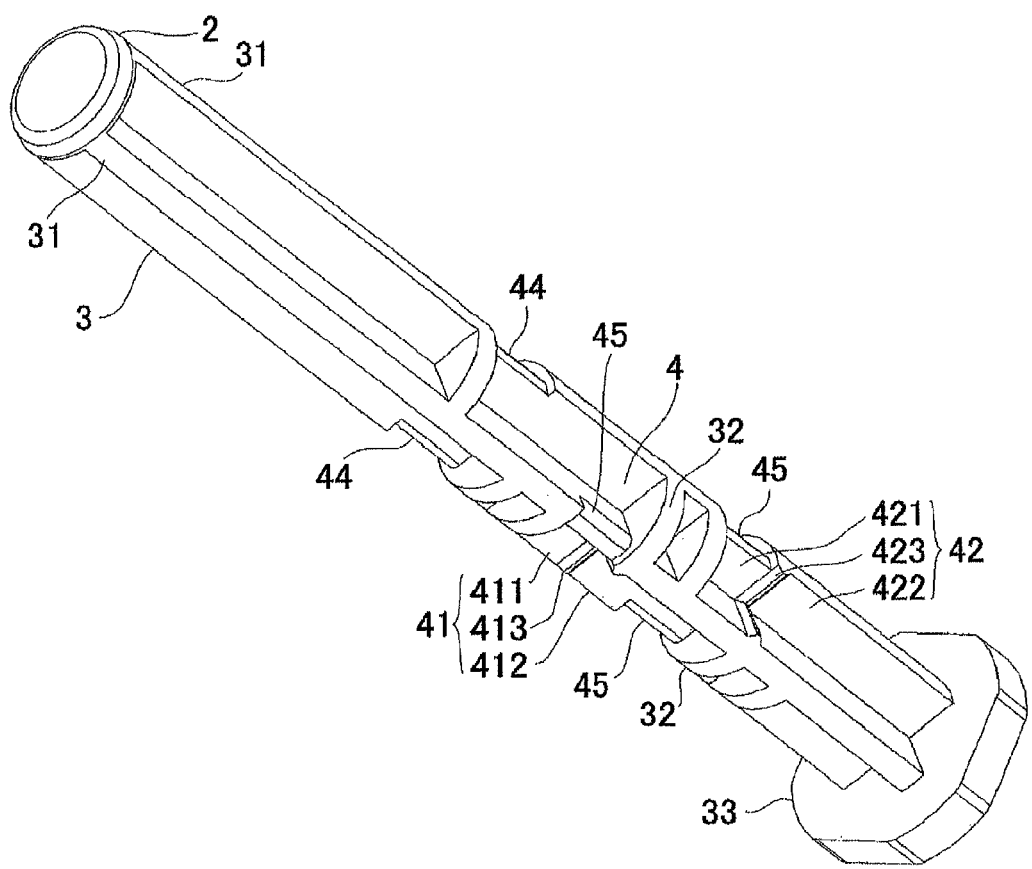
FIG. 5 is a perspective view showing the rod of FIG. 3 from the tip end side.
Figure 6:
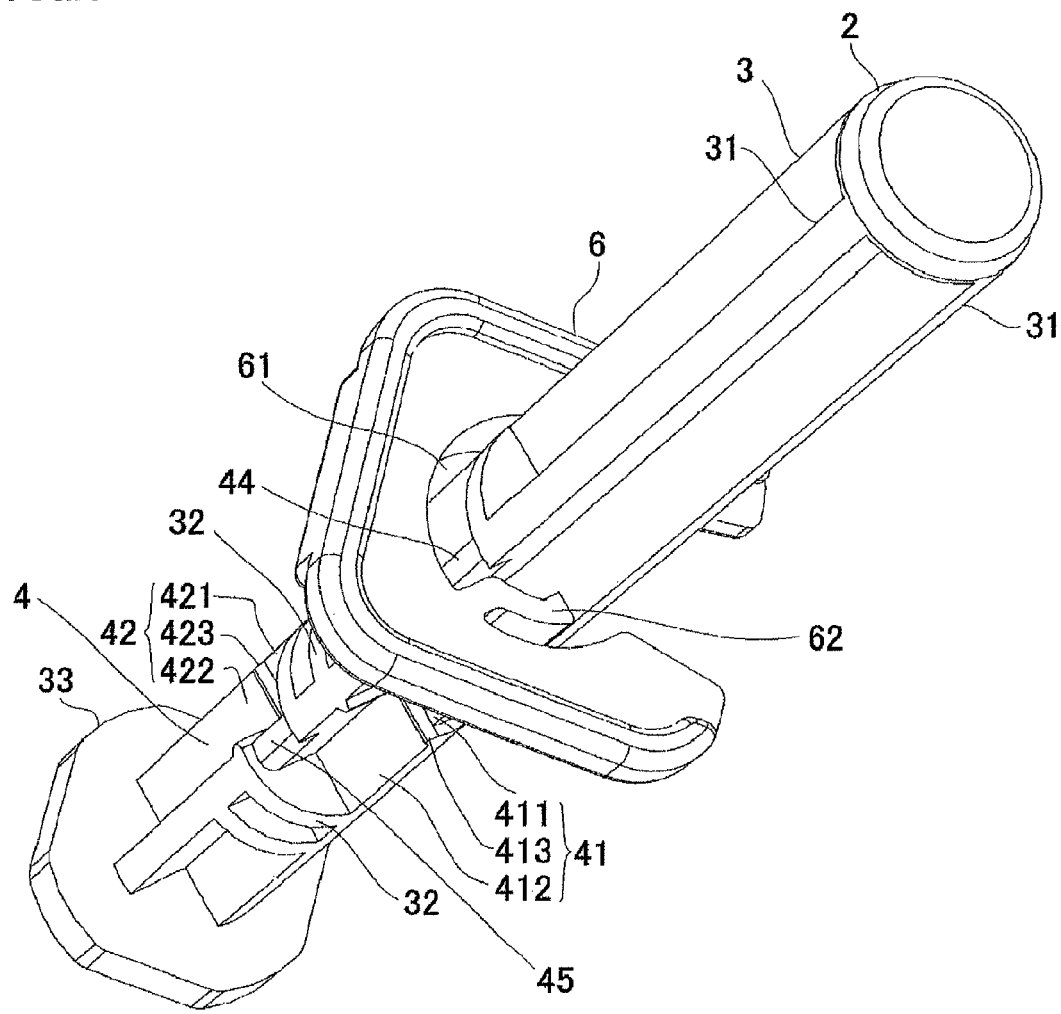
FIG. 6 shows only the relation between the rod and a regulating member of the spraying device shown in FIG. 1.
Figure 7:
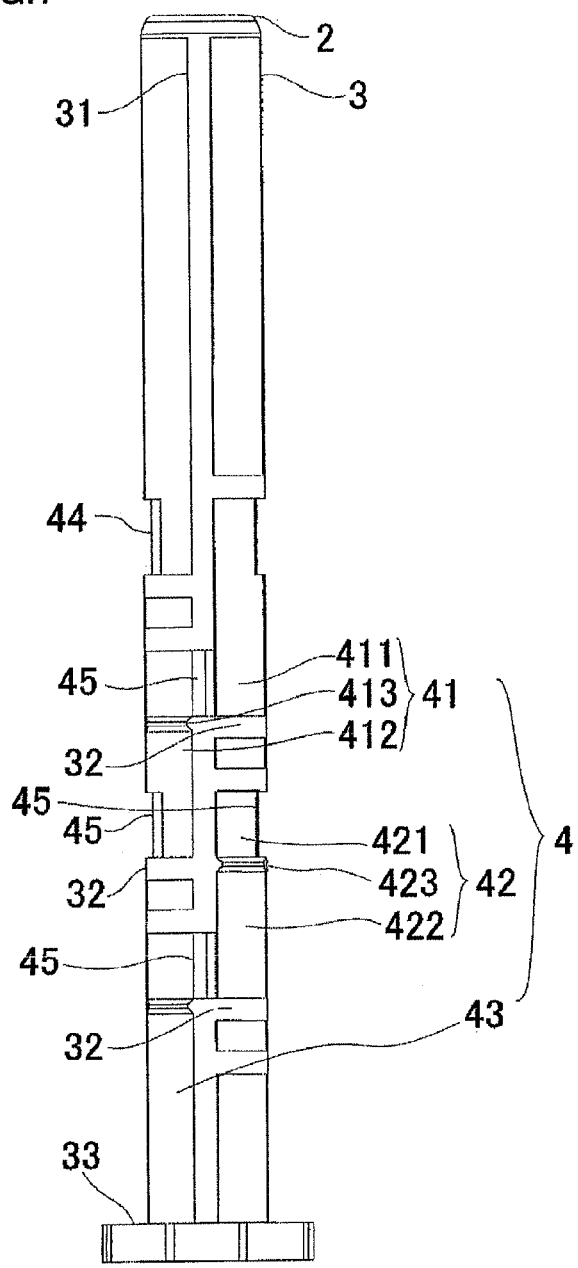
FIG. 7 is a perspective view of the rod having a third administering groove.

Rod 3 of the spraying device illustrated in FIG. 1 will further be described with reference to FIGS. 4 to 6, and regulating member 6 will further be described with reference to FIG. 7. Guide grooves 4 on rod 3 are formed in symmetry with respect to the central axis of rod 3, on the surface of rod 3 such that the pair of projections 62 formed on regulating member 6 can slide thereon. Projections 62 formed on regulating member 6, and guide grooves 4 may not be pairs as shown in these figures, and only one of each may be sufficient. Formation as a pair is preferred, however, since more stable movement of rod 3 is realized. Further, on rod 3, a portion with reduced diameter 44 is formed continuous from the tip end side of first administering groove 41, and regulating member 6 is attached through the portion of reduced diameter 44 when it is attached to barrel 1. The portion with reduced diameter serves as a lock when the spraying device is stored or when it is not immediately used.

It is a typical practice of nasal administration to spray medicament material of the same amount to both nasal cavities. Therefore, the first and second administering grooves 412 and 422 are formed to have the same length. If the spraying device is to be used for a treatment in which dosage differs in the first and second administrations, the first and second administering grooves 412 and 422 may be formed appropriately in different lengths to correspond to the different dosages.

Figure 3:
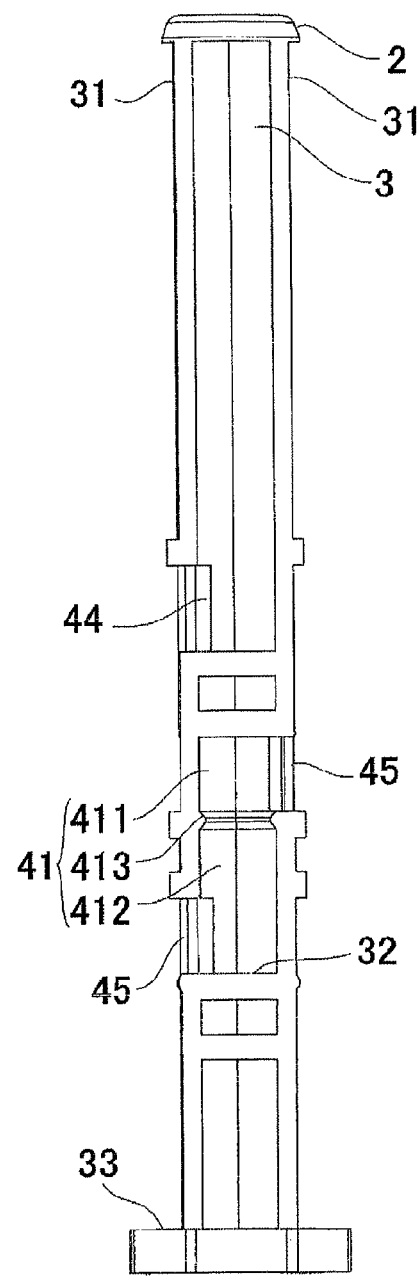
FIG. 3 is a front view of the rod provided in the spraying device of FIG. 1.

As shown in FIG. 3, rod 3 is provided with main ribs 31 at every 90 degrees on its cross-section, extending in the longitudinal direction of rod 3. Further, as shown in FIG. 7, regulating member 6 has arch-shaped columnar projections 62 each formed slidable along the adjacent main rib, such that each projection is accommodated between adjacent main ribs 31 and has the same diameter as the protruding position of main rib 31 with a circle about the rod axis as a reference. Further, on rod 3, at a bent point where the priming portion 411 as an L-shaped groove changes its direction from the longitudinal direction to the circumferential direction and at the base ends of the first and second administering portions 412 and 422, circumferential ribs 32 are formed. Once projection 62 abuts circumferential rib 32, rod 3 cannot further be pushed to the tip end direction as it is.

One of two adjacent main ribs 31 protrudes lower at a portion where it is in contact with circumferential rib 32, so that arch-shaped columnar projection 62 can overcome this portion. This portion of lower projection serves as the protrusion 45 for preventing rotation, which prevents rotation of rod that is not intended by the user. Though provision of rotation preventing protrusion 45 is preferred for higher safety of use, rotation preventing protrusion 45 is not absolutely necessary. As to the rib of lower projection, the rib itself may not be formed at this portion, and the rib may not exist here.

At the boundary between the priming portion 411 and the first administering portion 412 and at the boundary between transitional portion 421 and the second administering portion 422, that is, at the same positions as the circumferential ribs in terms of the longitudinal direction, energizing protrusions 413 and 423 as small projections are formed. Energizing protrusions 413 and 423 are of such a size that is sufficient to temporarily stop projection 62, to prevent pushing of rod 3 to the tip end direction. This prevents unintended spraying and ensures spraying of a desired amount. Energizing protrusions 413 and 423 are of such a size that, when projection 62 abuts energizing protrusions 413 and 423, projection 62 can move over these protrusions when rod 3 is pushed with force toward the tip end, and this force generates the pressure for spraying. Energizing protrusions 413 and 423 have the function of preventing unintended spraying and the function of applying pressure for spraying. Specifically, it has the effect of preventing discharge of liquid not in the atomized state that occurs when the rod is pushed weakly. The first energizing protrusion is provided at the position of initial spraying and, depending on the shape of priming portion, delicate operation is unnecessary. Therefore, it is not absolutely necessary. Its provision, however, is preferred from the viewpoint of spraying.

Figure 8:
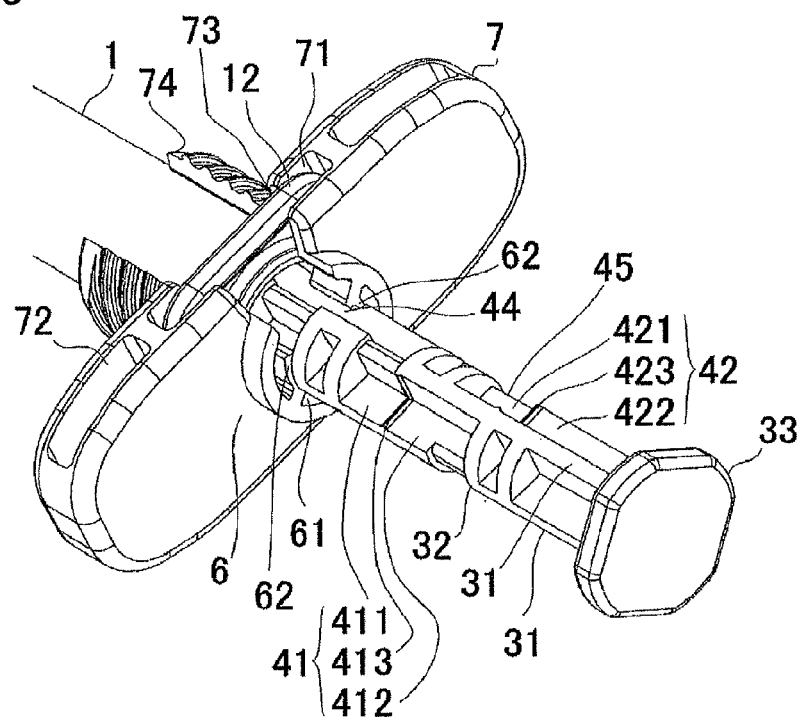
FIG. 8 is an enlarged perspective view showing the base end side of the spraying device with a finger flange member.

The foregoing are examples of the regulating member and the guide grooves, and not specifically limiting. An approach may be possible in which linear guide grooves are formed on a columnar rod and columnar projections that can slidably fit with the linear guide grooves are formed on the regulating member. The rod rotating operation may not be by 90 degrees. Further, though first and second administering grooves are provided in the example above, a plurality of additional administering grooves, such as third and fourth administering grooves, may be provided. The plurality of administering grooves may be added by realizing the same continuing relation between the first and second administering grooves. As a representative, rod 3 having the third administering groove is shown in FIG. 8.

Figure 9:
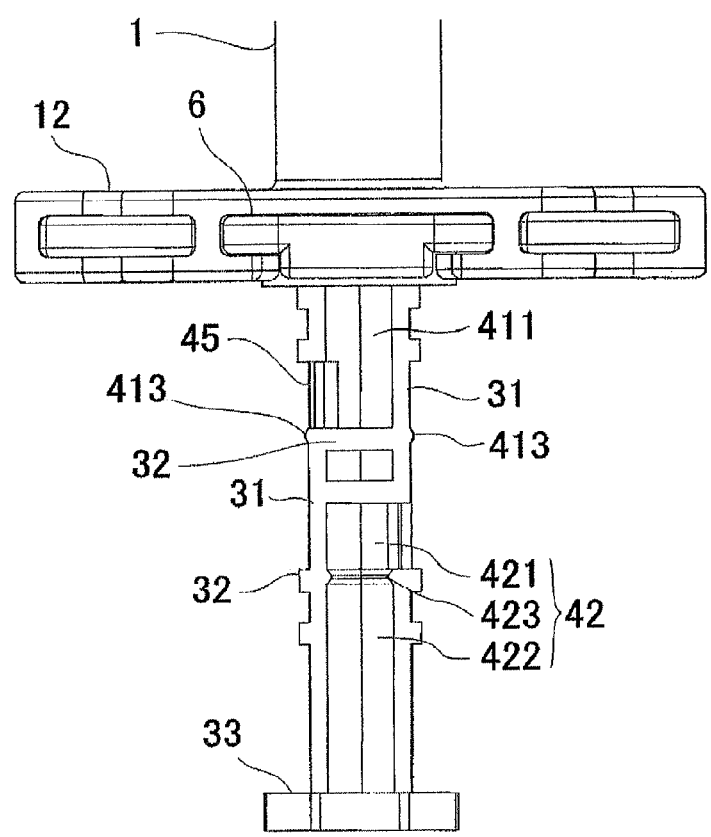
FIG. 9 is an enlarged front view showing the base end side of the spraying device of FIG. 1 in a storage state.

As to regulating member 6, though an example in which it is inserted to regulating member housing 13 formed on flange 12 has been described, regulating member 6 may be attached to the outside of flange 12. Specifically, the base end of barrel 1 may be covered from outside with a finger flange member 7, which is provided with regulating member 6 having a flat, plate-like C-shape, as shown in FIG. 9. Finger flange member 7 can be implemented by providing a flange housing portion 71 capable of accommodating flange 12 therein on a surface of regulating member 6 on the tip end side, and by forming a top panel 72 of flange housing portion 71 in the same C-shaped flat plate opened at the same position as regulating member 6 so that it can be engaged with the outer wall of barrel 1. The opening of top panel 72 serves as a fixing portion 73 and prevents slipping of finger flange member 7 from barrel 1. A C-shaped columnar body 74 opened at the same position as top panel 72 may be formed on the surface of top panel 72 on the tip end side.

Spray nozzle 5 has a spray opening 51 for spraying medicament at its tip end and a pair of overhanging pieces 52 at its base end, and it is mounted on Leur Lock as spray nozzle connecting portion 11 at the barrel tip end. In spray nozzle 5, a pressure applying member 53 is provided, which narrows a flow path to increase pressure of the medicament in the barrel fed to spray nozzle 5 and thereby to apply spraying force. Spray nozzle 5 and spray nozzle connecting portion 11 are coupled by Leur Lock and, therefore, spray nozzle 5 does not come off from barrel 1 even when pressure is applied at the time of spraying.

Figure 16:
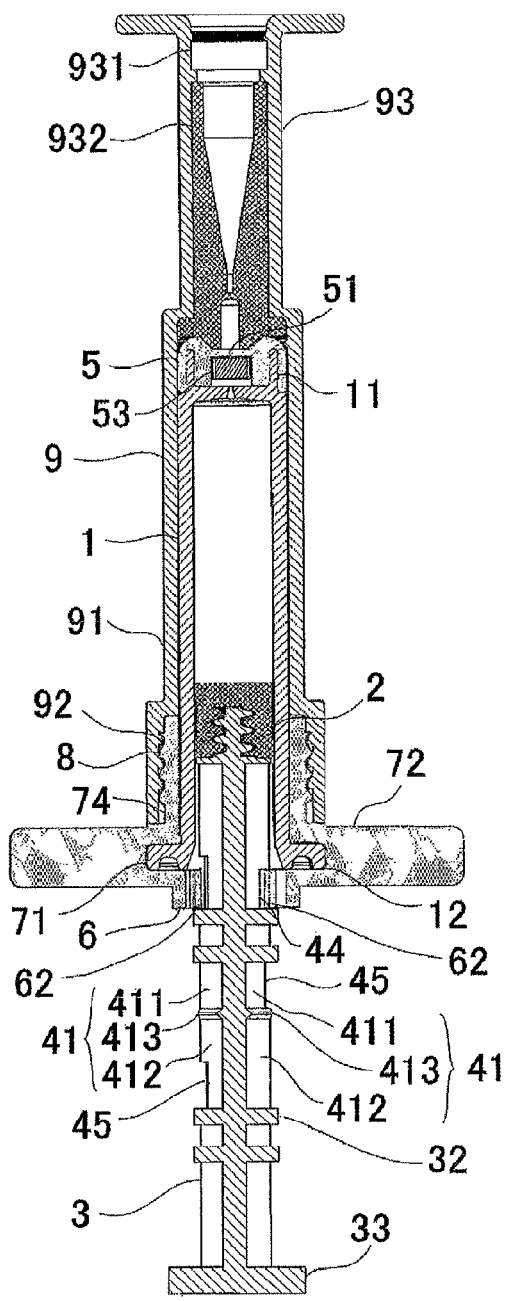
FIG. 16 is a vertical sectional view of the spraying device provided with a container adaptor for connecting a syringe.

Though Leur Lock is described as an exemplary method of mounting spray nozzle 5 on spray nozzle connecting portion 11, it is not limiting and any method may be used provided that connection is ensured at the time of spraying. The shape of nozzle is not limiting, either, and, by way of example, it may have such a shape as shown in FIG. 16.

Figure 10:
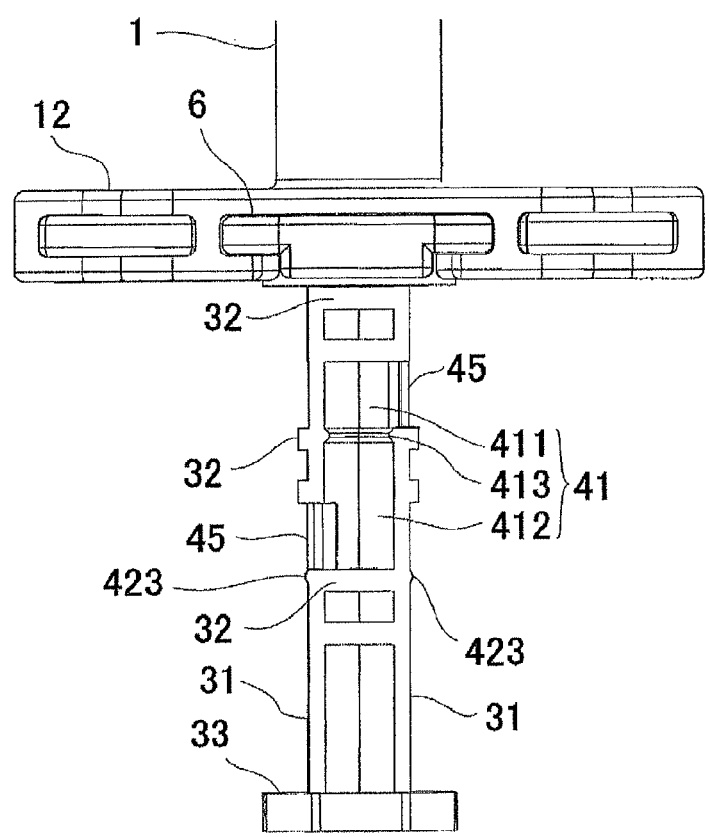
FIG. 10 is an enlarged front view showing the base end side of the spraying device of FIG. 1 in use.
Figure 11:
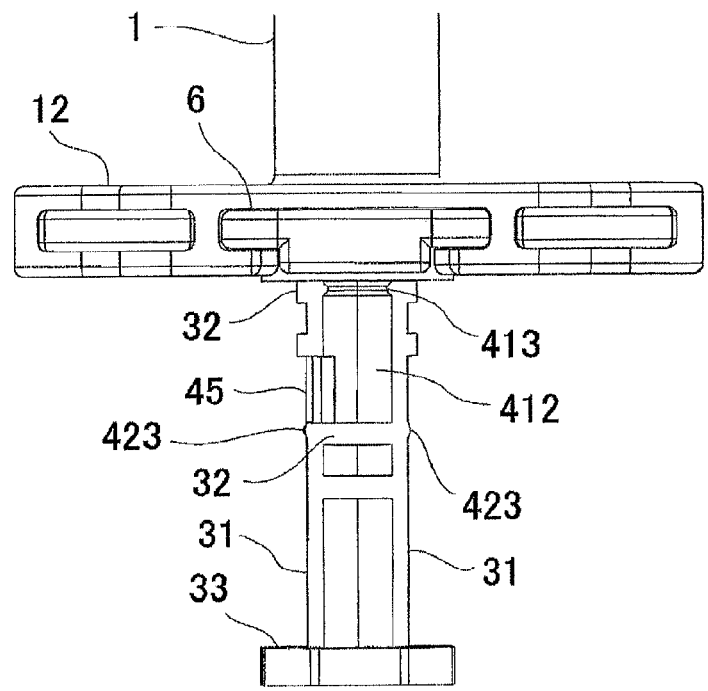
FIG. 11 is an enlarged front view showing the base end side of the spraying device of FIG. 1 at the completion of priming.
Figure 12:
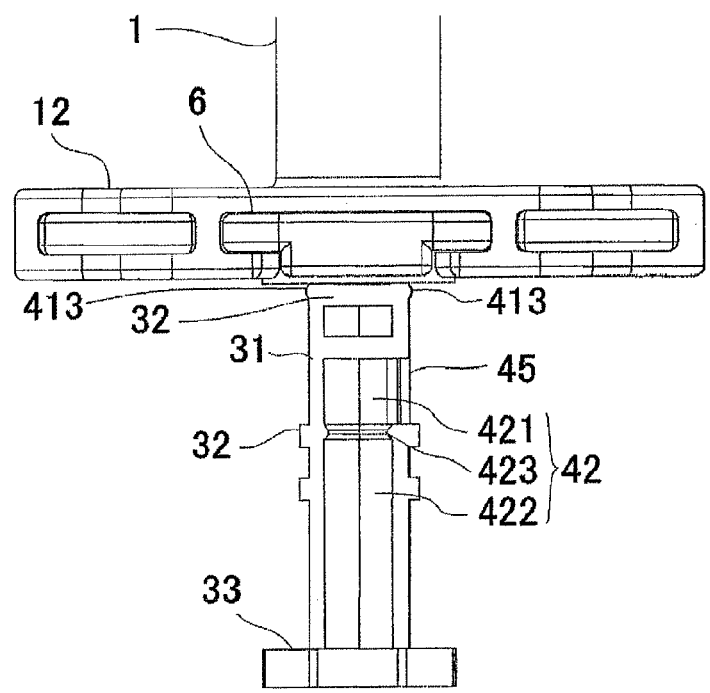
FIG. 12 is an enlarged front view showing the base end side of the spraying device of FIG. 1 ready for spraying.

A basic method of use will be described with reference to the spraying device of FIG. 1. First, the device is set, from a locked state shown in FIG. 9, to a usable state by a rotation of 90° (FIG. 10). The plunger is pushed for a priming operation until projection 62 abuts base end in the longitudinal direction of priming portion 411, so that the spraying device is filled with medicament (FIG. 11). Thereafter, rod 3 is rotated by 90° to overcome rotation preventing protrusion 45 adjacent to projection 62, and thus, the device is ready for administration. FIG. 12 shows the administration ready state. Here, movement of rod 3 to the tip end direction is regulated by first energizing protrusion 413 and, therefore, unintended dripping or leakage of liquid can be prevented.

Figure 13:
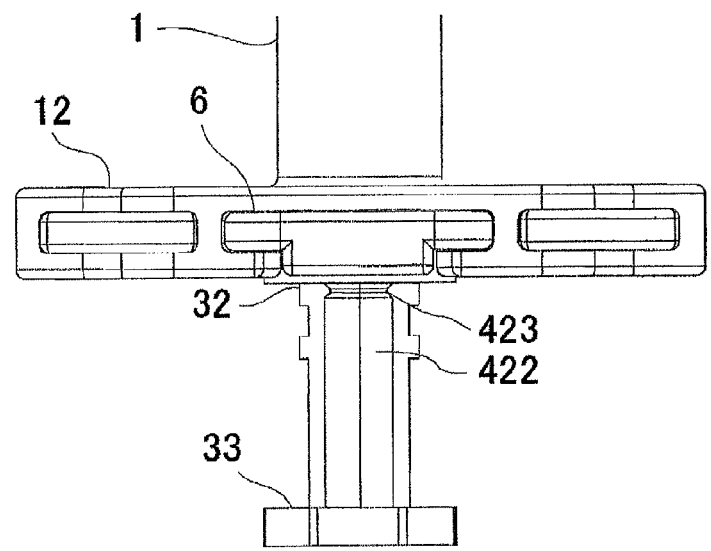
FIG. 13 is an enlarged front view showing the base end side of the spraying device of FIG. 1 at the completion of the first spraying.

Next, rod 3 is pushed with force until it abuts circumferential rib 32 to have projection 62 go over the first energizing protrusion 413, whereby the first spraying is completed (FIG. 13). Here, in order to force projection 62 go over energizing protrusion 413, strong pushing is necessary and, by this operation, thrust necessary for spraying is also attained. Accordingly, spraying failure (dripping of liquid) resulting from insufficient thrust can be avoided.

Figure 14:
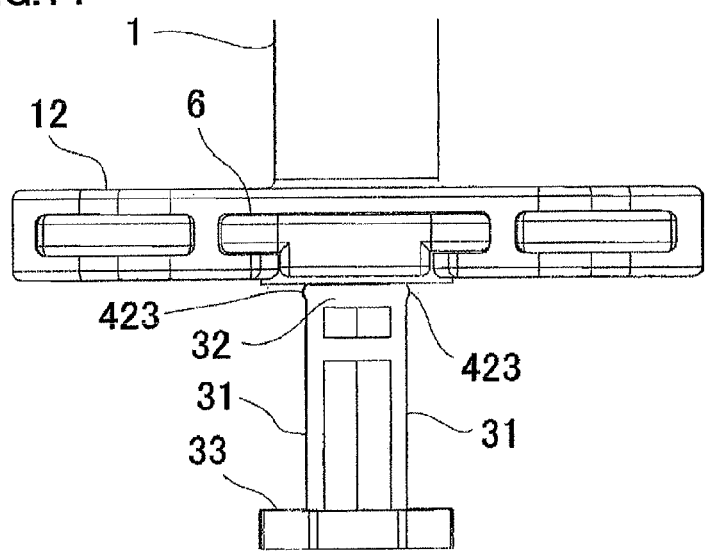
FIG. 14 is an enlarged front view showing the base end side of the spraying device of FIG. 1 ready for the second spraying.
Figure 15:
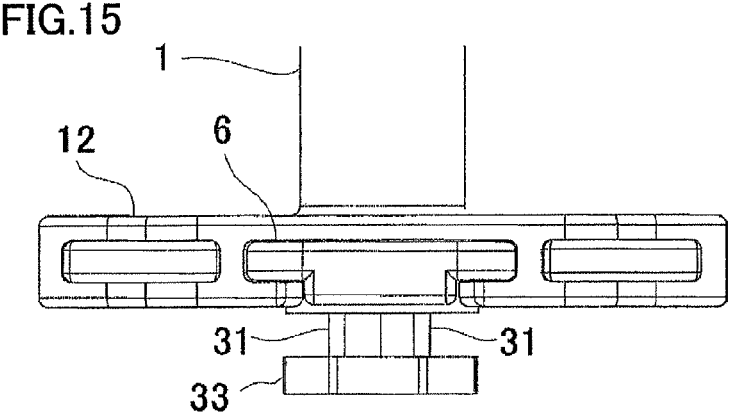
FIG. 15 is an enlarged front view showing the base end side of the spraying device of FIG. 1 at the completion of the second spraying.

After the completion of first spraying, in order to enable the second spraying, rod 3 is rotated such that projection 62 goes over rotation preventing protrusion 45 and enters transitional portion 421, until projection 62 abuts main rib 31 (FIG. 14). Here, the base end side of projection 62 abuts the second energizing protrusion 423. Similar to the first energizing protrusion 413, the second energizing protrusion 423 also serves to regulate movement of rod 3 in the direction toward the tip end. Then, the rod is fully pushed with force until it abuts base end rib 33 to have projection 62 go over the second energizing protrusion 423, whereby the second spraying is completed (FIG. 15).

Another embodiment, in which the device is used with medicament transferred from another container, will be described with reference to FIG. 16. A hollow barrel 1 has a fit-type spray nozzle connecting portion 11 formed at a tip end, and has a flange 12 at a base end. To spray nozzle connecting portion 11, a spray nozzle 5 is connected. In barrel 1, a gasket 2 that can slide and move in liquid-tight manner in barrel 1 is provided, and a rod 3 is coupled to the base end of gasket 2. A guide groove 4 is formed on rod 3, and guide groove 4 includes a first administering groove 41 and a second administering groove 42. The first administering groove is configured to include an L-shaped priming portion 411 extending from the tip end side along the longitudinal direction and then circumferential direction, and a first administering portion 412 extending from the base side end of a pre-administering portion along the longitudinal direction to the base end. At the boundary between priming portion 411 and the first administering portion 412, a first energizing protrusion 413 is formed. The second administering groove 42 is formed continuous from the first administering portion 412. The second administering groove 42 is configured to include a transitional portion 421 extending in the circumferential direction and having a groove wall on the base end side aligned with the base end of the first administering portion 412, and a second administering portion 422 extending from the transitional portion 421 along the longitudinal direction to the base end. At the boundary between transitional portion 421 and the second administering portion 422, a second energizing protrusion 423 is formed. On the base end of barrel 1, a finger flange member 7, which is provided with regulating member 6 having a flat, plate-like C-shape at its base end is mounted, covering from outside the base end of barrel 1. Finger flange member 7 is provided with a flange housing portion 71 capable of accommodating flange 12 therein on a surface of regulating member 6 on the tip end side. A top panel 72 of flange housing portion 71 is formed in the same flat, plate-like C-shape opened at the same position as regulating member 6, which can be engaged with the outer wall of barrel. On a surface on the tip end side of top plate 72, a C-shaped columnar body 74 opened at the same position as top plate 72 is formed, and on an outer circumferential surface of C-shaped columnar body 74, a thread as an adaptor mounting portion 8 is formed. A pair of arch-shaped columnar projections 62 that can slidably fit with the guide grooves 4 is formed, protruding from an edge of opening 61 to the central portion, to be opposite to each other, on regulating member 6.

A medicament container adapter 9 is mounted on and covers from outside the barrel to which spray nozzle 1 is attached. Medicament container adapter 9 includes a barrel covering portion 91 having a coupling portion 92 that can be coupled with adapter mounting portion 8 at the base end, and a container connecting portion 93 that communicates in liquid-tight manner with the spray nozzle at the tip end.

Though adapter mounting portion 8 is provided on the outer wall of C-shaped columnar body 7 in the example above, what is necessary is that it is provided in a detachable manner from outside of the barrel to cover barrel 1. Therefore, even if the device is of the type not provided with finger flange member 7 such as shown in FIG. 1, container adapter 9 can be applied by forming adaptor mounting portion 8 on the barrel outer wall.

FIG. 16 shows an example in which another syringe is connected as container adapter 9. Here, a container connecting portion 93 has a syringe receptor opening 931 and a rubber cap 932 having a conically shaped recess, as a cone facing downward to the base end, provided liquid-tight inside the syringe receptor opening 931. When a syringe with a needle containing medicament therein is inserted to syringe receptor opening 931 and the needle punctures rubber cap 932, the medicament in the syringe can be transferred to the spraying device in aseptic condition. A vaccine or the like produced to be administered by injection can be administered by spraying, by using medicament container adapter 9.

Figure 17:
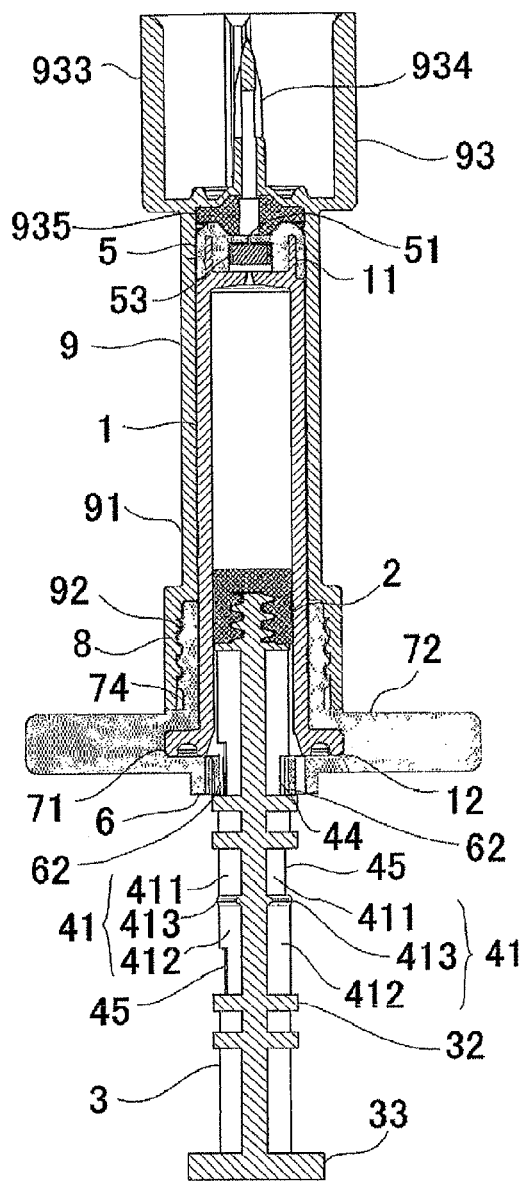
FIG. 17 is a vertical sectional view of the spraying device provided with a container adaptor for connecting a vial.
Figure 18:
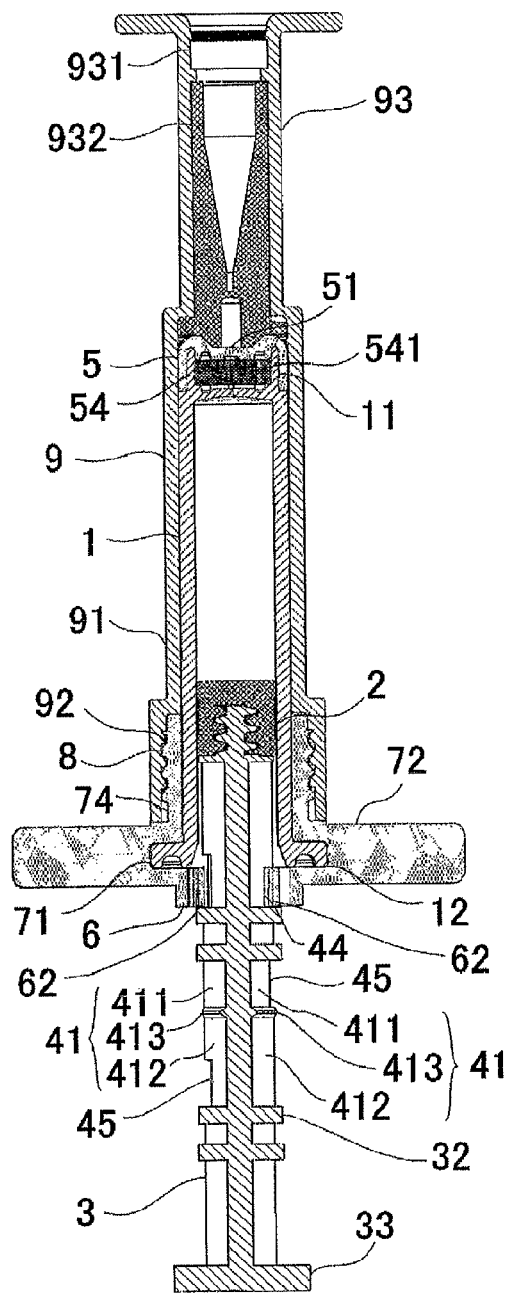
FIG. 18 is a vertical sectional view of the spraying device provided with a disk on a spray nozzle of FIG. 16.

Besides the syringe, an example of the type in which a vial is connected is also possible, as shown in FIG. 17. Container connecting portion 93 is provided with a hood 933 for attaching a vial, and has a communicating needle 934 therein, which needle is communicating in liquid-tight manner with the spray nozzle at the base end and is capable of puncturing a rubber plug of vial at its tip end. Between the communicating needle and the spray nozzle, a packing 935 is provided. This enables transfer of medicament liquid in the vial to the spraying device.

As variation of the spraying device provided with such container adapter 9, a disk 54 having freeze-dried formulation sealed therein and having a hole 541 communicated with spray nozzle 5 and barrel 1 may be provided in spray nozzle 5, as shown in FIG. 18. Since medicament can be stored in freeze-dried state, stable storage is possible. Further, by introducing a solution for reconstitution to barrel 1 by connecting a syringe or vial having the solution sealed therein, the solution flows through disk 54 and, thus, preparation is easy. Further, the disk hole 541 increases the pressure of pushed medicament and improves spraying capability. Therefore, spraying with disk 54 left as it is poses no problem.

As to the method of use when container adapter 9 as described above is provided, after the medicament (reconstituted solution) is filled from the medicament container to the spraying device, container adapter 9 is removed, and then, the spraying device can be used in the similar manner as described in the foregoing (0030).

INDUSTRIAL APPLICABILITY

As described above, the spraying device in accordance with the present invention allows spraying of a prescribed, equal amount of medicament a number of times, simply by pushing a rod. Therefore, it can suitably be used for medical applications.

REFERENCE SIGNS LIST

1 barrel
11 spray nozzle connecting portion
12 flange
13 regulating member housing
2 gasket
3 rod
31 main rib
32 circumferential rib
33 base end rib
4 guide groove
41 first administering groove
411 priming portion
412 first administering portion
413 first energizing protrusion
42 second administering groove
421 transitional portion
422 second administering portion
423 second energizing protrusion
43 third administering groove
44 portion with reduced diameter
45 rotation preventing protrusion
5 spray nozzle
51 spray opening
52 overhanging piece
53 pressure applying member
54 disk
541 disk hole
6 regulating member
61 opening
62 projection
7 finger flange member
72 top panel
73 barrel fixing portion
74 C-shaped columnar body
8 adapter mounting portion
9 container adapter
91 barrel covering portion
92 coupling portion
93 container connecting portion
931 syringe receptor opening
932 rubber cap
933 hood
934 communicating needle
935 packing

The invention claimed is:

1. A spraying device for spraying liquid, comprising:
a hollow barrel having a spray nozzle mounting portion formed at a tip end and a flange formed at a base end;
a gasket provided slidably movable in liquid-tight manner in said barrel;
a rod coupled to a base end of the gasket;
a guide groove provided on said rod; and
a regulating member, provided on said barrel, having an opening allowing passage of the rod formed at the center, and having a projection projecting from an edge of the opening to the center to be slidably fit with said guide groove, wherein
said guide groove includes at least a first administering groove and a second administering groove provided continuous from said first administering groove;
said first administering groove is configured to include a priming portion and a first administering portion extending from said priming portion to a base end along the longitudinal direction;
said second administering groove is configured to include a transitional portion extending in the circumferential direction with a groove wall on the base end side aligned with the base end of said first administering portion, and a second administering portion extending from the transitional portion to the base end along the longitudinal direction,
an energizing protrusion engageable with said projection is provided at a boundary between said transitional portion and said second administering portion, said energizing protrusion extending in two directions at the boundary to define a substantially right angle member,
a minimum radial extent of the regulating member is less than an internal radius of the hollow barrel, and
the rod is configured to be rotatable between the first and second administering portions.

2. The spraying device according to claim 1, wherein the priming portion is a groove extending in the longitudinal direction, a groove extending in a circumferential direction, or an L-shaped groove having a tip end side extending in the longitudinal direction and a base end side extending in the circumferential direction.

3. The spraying device according to claim 1, wherein an energizing protrusion engageable with said projection is provided at a boundary between said priming portion and said first administering portion.

4. The spraying device according to claim 1, wherein a rotation preventing protrusion engageable with said projection is further provided at a boundary between said first and second administering grooves.

5. The spraying device according to claim 1, wherein said guide groove further includes a third administering groove, said third administering groove is configured to include a transitional portion extending in the circumferential direction with a groove wall on the base end side aligned with the base end of said second administering portion, and a third administering portion extending from the transitional portion to the base end along the longitudinal direction; and
a third energizing protrusion engageable with said projection is provided at a boundary between said transitional portion and said third administering portion.

6. A spraying device for spraying liquid, comprising:
a hollow barrel having a spray nozzle mounting portion formed at a tip end and a flange formed at a base end;
a gasket provided slidably movable in liquid-tight manner in said barrel;
a rod coupled to a base end of the gasket;
a guide groove provided on said rod; and
a regulating member, provided on said barrel, having an opening allowing passage of the rod formed at the center, and having a projection projecting from an edge of the opening to the center to be slidably fit with said guide groove, wherein
said guide groove includes at least a first administering groove and a second administering groove provided continuous from said first administering groove,
said first administering groove is configured to include a priming portion and a first administering portion extending from said priming portion to a base end along the longitudinal direction,
said second administering groove is configured to include a transitional portion extending in the circumferential direction with a groove wall on the base end side aligned with the base end of said first administering portion, and a second administering portion extending from the transitional portion to the base end along the longitudinal direction,
an energizing protrusion engageable with said projection is provided at a boundary between said transitional portion and said second administering portion,
said energizing protrusion extending in two directions at the boundary to define a substantially right angle member,
said flange has a housing portion capable of accommodating said regulating member, and said regulating member is housed in said housing portion, and
the rod is configured to be rotatable between the first and second administering portions.

7. A spraying device for spraying liquid, comprising:
a hollow barrel having a spray nozzle mounting portion formed at a tip end and a flange formed at a base end;
a gasket provided slidably movable in liquid-tight manner in said barrel;
a rod coupled to a base end of the gasket;
a guide groove provided on said rod; and
a regulating member, provided on said barrel, having an opening allowing passage of the rod formed at the center, and having a projection projecting from an edge of the opening to the center to be slidably fit with said guide groove, wherein
said guide groove includes at least a first administering groove and a second administering groove provided continuous from said first administering groove;
said first administering groove is configured to include a priming portion and a first administering portion extending from said priming portion to a base end along the longitudinal direction;
said second administering groove is configured to include a transitional portion extending in the circumferential direction with a groove wall on the base end side aligned with the base end of said first administering portion, and a second administering portion extending from the transitional portion to the base end along the longitudinal direction,
an energizing protrusion engageable with said projection is provided at a boundary between said transitional portion and said second administering portion,
said energizing protrusion extending in two directions at the boundary to define a substantially right angle member,
a minimum radial extent of the regulating member is less than an internal radius of the hollow barrel, and
said regulating member further has, at a tip end, a housing portion capable of accommodating the flange therein, and a fixing portion engageable with an outer wall of the barrel, and is attached by accommodating a lower end of the barrel.

8. The spraying device according to claim 1, wherein a spray nozzle is mounted on said spray nozzle mounting portion.

9. The spraying device according to claim 8, wherein said spray nozzle contains powdered formulation.

10. The spraying device according to claim 1, further having a medicament container adapter allowing communication between the barrel and another medicament container, detachably provided to cover the barrel.

11. The spraying device according to claim 2, wherein an energizing protrusion engageable with said projection is provided at a boundary between said priming portion and said first administering portion.

12. The spraying device according to claim 2, wherein a rotation preventing protrusion engageable with said projection is further provided at a boundary between said first and second administering grooves.

13. The spraying device according to claim 3, wherein a rotation preventing protrusion engageable with said projection is further provided at a boundary between said first and second administering grooves.

14. The spraying device according to claim 2, wherein said guide groove further includes a third administering groove, said third administering groove is configured to include a transitional portion extending in the circumferential direction with a groove wall on the base end side aligned with the base end of said second administering portion, and a third administering portion extending from the transitional portion to the base end along the longitudinal direction; and a third energizing protrusion engageable with said projection is provided at a boundary between said transitional portion and said third administering portion.

15. The spraying device according to claim 3, wherein said guide groove further includes a third administering groove, said third administering groove is configured to include a transitional portion extending in the circumferential direction with a groove wall on the base end side aligned with the base end of said second administering portion, and a third administering portion extending from the transitional portion to the base end along the longitudinal direction; and
a third energizing protrusion engageable with said projection is provided at a boundary between said transitional portion and said third administering portion.

16. The spraying device according to claim 4, wherein said guide groove further includes a third administering groove, said third administering groove is configured to include a transitional portion extending in the circumferential direction with a groove wall on the base end side aligned with the base end of said second administering portion, and a third administering portion extending from the transitional portion to the base end along the longitudinal direction; and
a third energizing protrusion engageable with said projection is provided at a boundary between said transitional portion and said third administering portion.

17. The spraying device according to claim 2, wherein said flange has a housing portion capable of accommodating said regulating member, and said regulating member is housed in said housing portion.

18. The spraying device according to claim 3, wherein said flange has a housing portion capable of accommodating said regulating member, and said regulating member is housed in said housing portion.

19. The spraying device according to claim 4, wherein said flange has a housing portion capable of accommodating said regulating member, and said regulating member is housed in said housing portion.

20. The spraying device according to claim 5, wherein said flange has a housing portion capable of accommodating said regulating member, and said regulating member is housed in said housing portion.

21. The spray device according to claim 1, wherein an outer diameter of the rod at the priming portion is smaller than an outer diameter of the hollow barrel adjacent the flange.

22. The spray device according to claim 1, wherein the minimum radial extent is defined by the projection of the regulating member.

23. The spray device according to claim 1, wherein said projection of the regulating member is provided in plurality to provide a pair of projections projecting from the edge of the opening to the center to be slidably fit with said guide groove, and
a distance between said pair of projections is less than an internal radius diameter of the hollow barrel.

24. The spray device according to claim 6, wherein said projection of the regulating member is provided in plurality to provide a pair of projections projecting from the edge of the opening to the center to be slidably fit with said guide groove, and
a distance between said pair of projections is less than an internal radius diameter of the hollow barrel.

25. The spray device according to claim 7, wherein said projection of the regulating member is provided in plurality to provide a pair of projections projecting from the edge of the opening to the center to be slidably fit with said guide groove, and
a distance between said pair of projections is less than an internal radius diameter of the hollow barrel.

* * * * *